(12) United States Patent
Kanazirev et al.

(10) Patent No.: US 7,393,993 B1
(45) Date of Patent: Jul. 1, 2008

(54) METHOD FOR REMOVAL OF ACETYLENES FROM HYDROCARBON STREAMS

(75) Inventors: Vladislav I. Kanazirev, Des Plaines, IL (US); David E. Mackowiak, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 56 days.

(21) Appl. No.: 11/557,849

(22) Filed: Nov. 8, 2006

(51) Int. Cl.
*C07C 5/35* (2006.01)
(52) U.S. Cl. .................. 585/809; 585/254; 585/264; 585/256; 585/654
(58) Field of Classification Search ............... 585/256, 585/254, 264, 654, 809
See application file for complete search history.

(56) References Cited

U.S. PATENT DOCUMENTS

| | | | |
|---|---|---|---|
| 3,755,488 A | 8/1973 | Johnson et al. | 260/677 A |
| 3,792,981 A | 2/1974 | Hettick et al. | 23/288 R |
| 3,812,057 A | 5/1974 | Morgan et al. | 252/416 |
| 3,912,789 A | 10/1975 | Frevel et al. | 260/681.5 |
| 4,082,694 A | 4/1978 | Wennerberg et al. | 252/444 |
| 4,425,255 A | 1/1984 | Toyoda et al. | 502/38 |
| 4,440,956 A | 4/1984 | Couvillion | 585/260 |
| 5,332,705 A | 7/1994 | Huang et al. | 502/53 |
| 6,124,517 A | 9/2000 | Kaminsky et al. | 585/829 |

FOREIGN PATENT DOCUMENTS

JP 61050929 3/1986

*Primary Examiner*—Thuan D. Dang
(74) *Attorney, Agent, or Firm*—Mark Goldberg

(57) ABSTRACT

The process of the invention comprises contacting a hydrocarbon stream, comprising light olefins plus impurities such as acetylenes, in the absence of hydrogen with a supported copper catalyst, preferably CuO/alumina. The acetylene component undergoes a coupling reaction producing a diacetylene which can be more readily removed. Thus, the methylacetylene (MA) contaminant in liquid propylene yields at about 80° C. and 3792 kPa (550 psig) a significant amount dimethyl diacetylene (2,4-hexadiyne). Surprisingly, very little cyclization products are present. The process is useful for purification of olefin feeds. It can be used alone or in combination with known purification methods such as catalytic distillation or selective hydrogenation.

9 Claims, No Drawings

METHOD FOR REMOVAL OF ACETYLENES FROM HYDROCARBON STREAMS

FIELD OF THE INVENTION

The field of this invention relates to use of particulate beds in purification of relatively impure olefins such as are typically produced by thermal cracking of suitable hydrocarbon feedstocks. More particularly, this invention concerns purification by passing an olefinic process stream, containing small amounts of acetylenic impurities, carbon oxides and/or other organic components, which are typically impurities in cracked gas, through a particulate bed comprising a metal oxide supported on a high surface area carrier under conditions suitable for selective conversion of alkynes essentially in the absence of hydrogen. This invention is particularly useful where the olefin being purified is ethylene and/or propylene formed by thermal cracking of hydrocarbon feedstocks.

BACKGROUND OF THE INVENTION

Olefins, including ethylene and propylene, are converted into a multitude of intermediate and end products on a large scale, mainly into polymeric materials. Commercial production of olefins is mostly accomplished by the thermal cracking of hydrocarbons. Unfortunately, due to the very high temperatures involved, these commercial olefin producing processes also yield a substantial amount of the less desired acetylenic (alkyne) impurities such as acetylene, methylacetylene and $C_4$ alkynes which contaminate the target olefin streams and therefore need to be removed. The separation of the acetylenes from the olefins can considerably increase the plant cost. Propylene, for example, can contain several percent methylacetylene and propadiene (collectively referred to as "MAPD"). A selective hydrogenation (SH) reaction with hydrogen in presence of supported metal catalysts is the most common method for MAPD removal. In spite of significant progress over the years, this process has significant shortcomings such as the need for a source of hydrogen, the appearance of side products such as green oil and propane, and catalyst deactivation from impurities such as arsine or carbonyl sulfide.

Several methods are known for separation of an organic gas containing unsaturated linkages from gaseous mixtures. These include, for instance, cryogenic distillation, liquid adsorption, membrane separation and pressure swing adsorption in which adsorption occurs at a higher pressure than the pressure at which the adsorbent is regenerated. Cryogenic distillation and liquid adsorption are common techniques for separation of carbon monoxide and alkenes from gaseous mixtures containing molecules of similar size, e.g. nitrogen or methane. However, both techniques have disadvantages such as high capital cost and high operating expenses. For example, liquid adsorption techniques suffer from solvent loss and need a complex solvent make-up and recovery system.

Beside palladium and modified palladium, copper with some additives can be used also as a catalyst for selective hydrogenation as seen in U.S. Pat. No. 3,912,789 and U.S. Pat. No. 4,440,956. Kokai JP Number 50929-1968 describes a method of purifying vinyl compounds containing up to about 10 percent by weight of acetylenic compounds. In this method, acetylenic compounds were described as being adsorbed on an adsorption agent of 1-valent and/or 0-valent copper and/or silver supported on inert carrier such as Δ alumina, silica or active carbon. Separations described included 1000 ppm ethyl acetylene and 1000 ppm vinyl acetylene from liquid 1,3-butadiene, 100 ppm acetylene from ethylene gas, 100 ppm methylacetylene from propylene gas, and 50 ppm phenyl acetylene from liquid styrene (vinylbenzene). Each application used fresh adsorption agent and only a short time of one hour on stream at mild conditions of temperature and pressure. Such limited applications were likely because it is well known that acetylene and these acetylene compounds react with copper and/or silver to form copper acetylide or silver acetylide. Both the acetylide of copper and silver are unstable compounds. Because they are explosive under some conditions, their possible formation presents safety problems in operation and in handling adsorbent containing such precipitates. A current commercial process employs a copper based catalyst in the presence of hydrogen.

It is known that acetylenic impurities can be selectively hydrogenated and thereby removed from such product streams by passing the product stream over an acetylene hydrogenation catalyst in the presence of dihydrogen (molecular hydrogen, $H_2$). However, these hydrogenation processes typically result in the deposition of carbonaceous residues or "green oil" on the catalyst which deactivates the catalyst. Therefore, acetylene hydrogenation processes for treating liquid or liquefiable olefins and diolefins typically include an oxygenation step or a "burn" step to remove the deactivating carbonaceous residues from the catalyst, followed by a hydrogen reduction step to reactivate the hydrogenation catalyst. For example, see U.S. Pat. No. 3,755,488 to Johnson et al., U.S. Pat. No. 3,792,981 to Hettick et al., U.S. Pat. No. 3,812,057 to Morgan and U.S. Pat. No. 4,425,255 to Toyoda. However, U.S. Pat. No. 3,912,789 and U.S. Pat. No. 5,332,705 state that by using selected hydrogenation catalysts containing palladium, at least partial regeneration can be accomplished using a hydrogenation step alone at high temperatures of 316° to 371° C. (600° to 700° F.) and in the absence of an oxygenation step.

Selective hydrogenation of the about 2000 to 4000 parts per million (ppm) of acetylenic impurities to ethylene is generally a crucial operation for purification of olefins produced by thermal steam cracking. Typical of a small class of commercially useful catalysts are materials containing very low levels of an active metal supported on an inert carrier, for example a particulate bed having less than about 0.03% (300 ppm) palladium supported on the surface skin of carrier pellets having surface area of less than about 10 $m^2/g$.

Many commercial olefin plants using steam crackers use front-end acetylene converters, i.e. the hydrogenation unit is fed $C_3$ and lighter cracked gas, which has a high enough concentration of hydrogen to easily hydrogenate the acetylenic impurities; however, when run improperly, will also hydrogenate a large fraction of the ethylene and propylene product. Both hydrogenation of acetylene and ethylene are highly exothermic.

One technology used for removal of acetylenes is described in U.S. Pat. No. 6,124,517 assigned to BP Amoco.

This patent discloses the removal of acetylenes from olefin streams by adsorption in absence of hydrogen over a copper—alumina adsorbent containing Cu in a reduced, zero covalent state. Hydrogen containing gas is then used to regenerate the adsorbent.

The present invention provides an efficient method for purification of hydrocarbon streams, olefins in particular, by removing acetylenes from the hydrocarbon stream in the absence of hydrogen. The acetylenes are converted to a diacetylene form which can be easily separated from the hydrocarbon stream due to the high boiling and melting points of the diacetylenes. One of the possible applications of the present invention is as a pre-treatment in combination with a selective hydrogenation step in which the load on the selective hydrogenation unit is significantly reduced and allowing for the processing of a significantly greater sized hydrocarbon stream.

SUMMARY OF THE INVENTION

The present invention provides a low cost method for purification of hydrocarbon streams in the absence of hydrogen through the use of a metal oxide on a support, preferably a copper oxide—alumina catalyst. A significant advantage of the invention is that acetylenes are partially converted to the corresponding olefins without production of saturated hydrocarbons. The diacetylene byproduct can be easily separated and utilized as a chemical. Such separations may be achieved through distillation, including reactive (catalytic) distillation, since the condensation products of acetylenic hydrocarbons have higher boiling point than the olefins.

Crystallization could be also used, as the melting point of the condensation product of methylacetylene and 2,4-hexadiyne is 68° C. The metal oxide—alumina catalyst that is applied serves at the same time as a guard bed to remove other contaminants such as oxygenates, arsine and carbonyl sulfide from olefins thereby providing protection to the catalysts of other processes downstream from this acetylene removal bed.

More specifically, the present invention is a process for purification of olefins comprising in an absence of added hydrogen passing a mixture comprising a hydrocarbon of from 2 to about 8 carbon atoms including at least one vinyl group, acetylenic impurities having the same or similar carbon content and, optionally, saturated hydrocarbon gases through a particulate bed comprising predominantly a support material having high surface area on which is dispersed a metal oxide, converting a portion of the acetylenic impurities to their corresponding condensation products such as diynes, while converting another portion of the acetylenic hydrocarbons to the corresponding olefins (alkenes) and thereby obtaining a purified effluent containing at least 50% less of the acetylenic impurities as compared to said gaseous mixture.

DETAILED DESCRIPTION OF THE INVENTION

The invention is based upon the reaction of acetylenes in presence of non-reduced metal oxide on a high surface area support, such as copper supported on alumina in particular. Other metal oxides can be used, such as palladium, silver, gold, zinc and cadmium. A number of support materials including alumina, silica, carbon, clay and zeolites (molecular sieves) can be used. Surface areas of support materials are, preferably, in a range of from about 10 to about 2,000 m$^2$/g as measured by the BET gas adsorption method. Alumina support materials are preferred for use in the present invention. Porous aluminas and transition aluminas are particularly preferred.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. Zeolitic materials are ordered porous crystalline aluminosilicates having a definite structure with large and small cavities interconnected by channels. The cavities and channels throughout the crystalline material are generally uniform in size allowing selective separation of hydrocarbons. A preferred class of active carbons useful herein are materials disclosed in U.S. Pat. No. 4,082,694. Such suitable active carbon products are produced from carbonaceous material by a staged temperature process which provides improved yield and processability during manufacture. Active carbon products for use as supports, according to this invention, preferably have an effective surface area greater than about 2,300 m$^2$/g, and more preferably greater than about 2,700 m$^2$/g, and most preferably above about 3,000 m$^2$/g as measured by the BET method. Active carbon products for use as supports typically have a bulk density greater than about twenty-five hundredths gram per cubic centimeter, and preferably greater than about twenty-seven hundredths gram per cubic centimeter, and more preferably above about three-tenths g/cc. Further, useful active carbon products preferably have a Total Organic Carbon Index greater than about 300, more preferably greater than about 500, and most preferably greater than about 700.

The reaction of the present invention consists of coupling (condensing) acetylenes predominantly to linear compounds containing less hydrogen accompanied by simultaneous production of olefins from the source acetylenic hydrocarbon. Nominally, the reaction can be regarded as a hydrogen transfer process if the hydrogen released by the coupling reaction serves to hydrogenate additional acetylene molecules. For example, three molecules of methylacetylene would produce one molecule of 2,4-hexadlyne (also known as dimethyldiacetylene or dimethylbutadiyne) and one molecule of propylene.

$$3C_3H_4 = C_6H_6 + C_3H_6 \quad (1)$$

Generally, other coupling products with even lower hydrogen content could be still possible thereby increasing the potential for generating olefins from acetylenes. Equation 2 shows potential route of advanced hydrogen disproportion reaction with methylacetylene.

$$4C_3H_4 = C_6H_4 + 2C_3H_6 \quad (2)$$

The potential product of such a reaction would be Hex-3-en-1,5-diyne.

The hydrocarbon that is treated comprises from 2 to about 8 carbon atoms, including at least one vinyl group, acetylenic impurities having the same or similar carbon content and optionally, saturated hydrocarbons. Preferably the hydrocarbon comprises olefins such as ethylene, propylene and butylene. The acetylenic impurities include acetylene, methylacetylene, propadiene and butynes. The purified effluent may be further treated by a selective hydrogenation reaction if higher purity is desired.

The following examples illustrate the invention.

EXAMPLE 1

This example describes the experimental setup used to study the methylacetylene and propadiene (collectively referred to herein as "MAPD") conversion in the presence of selected adsorbents or catalysts.

A Parr autoclave was equipped with a 300 cc vessel, a mechanical stirrer rotated at about 500 rpm, catalyst mesh basket with approximate volume of 37 cc and a liquid recycle loop operated by a designated pump. The autoclave was outfitted with pressure measurement and temperature control while the recycling liquid was analyzed "on-line" by a GC chromatograph using a PLOT capillary column capable of separating MAPD, propylene and other hydrocarbons.

A liquid blend containing approximately 96.6 mass-% propylene ($C_3^=$); 0.3% propane ($C_3$); 1.6% methylacetylene (MA) and 1.5% propadiene (PD) was used in all experiments. In a typical run, 25 g catalyst were loaded into the catalyst basket and purged with $N_2$ after sealing and leak testing of the autoclave. About 75 g (~120 cc) of the liquid blend were then introduced into the autoclave to react at room temperature under constant stirring. The temperature was then stepwise increased while the liquid phase was analyzed by GC every 30 minutes.

EXAMPLE 2

The materials tested are listed in Table 1. Each of the samples that were used were commercially used catalysts or adsorbents containing metal oxides or metals.

TABLE 1

| Sample | Active component, Mass-% | Size, mesh |
|---|---|---|
| 1 | Alpha alumina - no active component | 10-20 beads |
| 2 | CuO; ~30% | 7 × 14 beads |
| 3 | CuO~11% | 7 × 14 beads |
| 4 | CuO~10% | 7 × 14 beads |
| 5 | Cu, Ni, Zn~total 80% | 1/16" extrudates |
| 6 | NiO~78% | 1/16" extrudates |
| 7 | Ni~58% | 1/16" extrudates |

Table 2 summarizes the data with the samples listed in Table 1. Practically no MAPD conversion was observed with alpha alumina, nickel oxide or nickel. Very little conversion was found with sample "5". In contrast, the Cu containing samples had a relative high activity. The conversion was the highest with the sample "2". Surprisingly, a high boiling compound identified as 2,4-hexadiyne was produced as the main product of MA conversion. Practically, no cyclization products were observed at the conditions used.

TABLE 2

|   | Description | Temp., °C. | Pressure psig | Time hours | Propylene Mass % | MA Mass % | PD Mass % | 2,4-Hexadiyne Mass % | Selectivity % MA to 2,4 |
|---|---|---|---|---|---|---|---|---|---|
| 1 | Alpha alumina | 90.4 | 667 | 20 | 96.44 | 1.67 | 1.45 | 0.00 | 0 |
| 2 | 32% CuO/Alumina | 79.3 | 561 | 20 | 97.22 | 0.22 | 1.33 | 0.74 | 46 |
| 3 | 11% CuO/Alumina | 80.6 | 555 | 17 | 97.13 | 0.94 | 1.21 | 0.21 | 13 |
| 4 | 10% CuO/Alumina | 86.3 | 601 | 20 | 97.11 | 0.88 | 1.34 | 0.17 | 11 |
| 5 | Cu-Zn-Ni/Support | 85.6 | 601 | 20 | 96.55 | 1.54 | 1.41 | 0.00 | 0 |
| 6 | NiO/Support | 86.0 | 610 | 17 | 96.47 | 1.60 | 1.41 | 0.00 | 0 |
| 7 | Ni/Support | 86.8 | 611 | 17 | 96.49 | 1.60 | 1.41 | 0.00 | 0 |

The conversion of propadiene was generally low as one can see from Table 2. On the other hand, the propylene concentration rose with all samples where methylacetylene conversion was observed. However, it is difficult to quantify the amount of propylene present because its distribution between the liquid and vapor phase may be affected by the newly formed 2,4-hexadiyne that has some unique properties as a compound. It has a melting point of about 69° C. and a boiling point of ~129° C., which are 50° to 60° higher than that of the closest $C_6H_6$ isomers like benzene.

The identification of 2,4-hexadiyne was done unambiguously by GC-MS, retention time and addition of pure 2,4-hexadiyne standard.

EXAMPLE 3

This example shows the kinetics of methylacetylene conversion with the copper oxide on alumina catalyst—sample "2".

TABLE 3

| Time, hours | 1 | 2 | 3 | 4 | 5 | 6 | 7 | 8 | 9 | 10 |
|---|---|---|---|---|---|---|---|---|---|---|
| Internal Temp.,° C. | 25 | 29 | 78 | 82 | 82 | 82 | 81 | 81 | 81 | 81 |
| Pressure, psig | 215 | 233 | 548 | 583 | 582 | 582 | 581 | 580 | 576 | 575 |
| Propane | 0.316 | 0.313 | 0.317 | 0.319 | 0.318 | 0.317 | 0.316 | 0.318 | 0.319 | 0.317 |
| Propylene | 96.55 | 96.53 | 96.49 | 96.73 | 96.82 | 96.90 | 96.90 | 96.96 | 97.01 | 97.04 |
| Methylacetylene | 1.531 | 1.505 | 1.389 | 0.934 | 0.773 | 0.660 | 0.586 | 0.514 | 0.462 | 0.419 |
| 2,4-Hexadiyne | 0.028 | 0.055 | 0.203 | 0.437 | 0.504 | 0.550 | 0.603 | 0.641 | 0.641 | 0.664 |

Temperature is an important factor whereas at least 60° to 70° C. is needed for speeding up the reaction. At a contact time of 7 hours, the rate of methylacetylene consumption is almost equal to that of 2,4-hexadiyne formation, especially if one includes the potential formation of propylene as a co-product. Therefore, the selectivity seems to be very high. Very little heavy compounds were found in the liquid product by GC method.

EXAMPLE 4

This example illustrates that the methylacetylene reaction to 2,4-hexadiyne resumes on the copper oxide catalyst, although with a slower rate, after refilling the autoclave with fresh feed.

TABLE 4

| | Time, hours | | | | |
|---|---|---|---|---|---|
| | 1 | 2 | 3 | 4 | 5 |
| Internal Temp., ° C. | 80 | 80 | 80 | 80 | 80 |
| Pressure, psig | 568 | 573 | 572 | 567 | 567 |
| Propane | 0.315 | 0.315 | 0.313 | 0.314 | 0.315 |
| Propylene | 96.177 | 96.292 | 96.338 | 96.427 | 96.442 |
| Methylacetylene | 1.522 | 1.362 | 1.290 | 1.141 | 1.093 |
| 2,4-Hexadiyne | 0.088 | 0.135 | 0.170 | 0.220 | 0.251 |

EXAMPLE 5

The spent copper oxide catalyst was analyzed by X-ray analysis for phase identification and carbon content by combustion after the extended run at the conditions of Example 1. No attempts were made to remove the organic residue from the spent sample by washing with solvents. Only about 1.5% carbon was found on the spent catalyst while the fresh one contained 0.36% carbon. Hence, it does not seem that the coke formation had a major impact on the product conditions at the conditions used.

X-ray data of both fresh and spent samples of the copper oxide catalyst found spectra peaks which are characteristic of CuO present in both fresh and spent sample "2". Hence, the formation of 2,4-hexadiyne has a catalytic nature. It is not due to a stoichiometric reaction between CuO and methylacetylene.

Selective hydrogenation is the only current commercial process for removal of acetylenes from olefinic streams. Although the process according to the present invention can be used as a separate process, one effective way to practice it is in front of the selective hydrogenation unit. Thus, the process of this invention would purify the feed by removing arsine and sulfur contaminants and in addition the methylacetylene content will be also significantly reduced. This would significantly reduce the load on the selective hydrogenation unit with a reduction in the consumption of hydrogen and the overall cost.

What is claimed is:

1. A process for purification of olefins which comprises:
    in an absence of added hydrogen, passing a mixture comprising olefins and a hydrocarbon of from 2 to about 8 carbon atoms including at least one vinyl group, acetylenic impurities having the same or similar carbon content and, optionally, saturated hydrocarbon through a particulate bed of catalyst comprising predominantly a support material having high surface area on which is dispersed a metal oxide selected from the group consisting of copper oxide, silver oxide, gold oxide, palladium oxide, zinc oxide, and cadmium oxide;
    converting a portion of said acetylenic impurities to their corresponding condensation products diynes while converting another portion of the acetylenic impurities to their corresponding olefins and thereby obtaining a purified effluent containing less of the acetylenic impurities as compared to said hydrocarbon mixture.

2. The process of claim 1 wherein said metal oxide is copper oxide.

3. The process of claim 1 wherein said support material is selected from the group consisting of alumina, silica, carbon, clay and zeolites.

4. The process of claim 3 wherein said support material is alumina.

5. The process of claim 1 wherein said hydrocarbon comprises olefins selected from the group consisting of ethylene, propylene and butylene.

6. The process of claim 1 wherein said catalyst functions to remove arsenic and sulfur impurities from said gaseous mixture.

7. The process of claim 1 wherein said catalyst functions to remove oxygenate impurities from said gaseous mixture.

8. The process of claim 1 wherein said acetylenic impurities are selected from the group consisting of acetylene, methylacetylene, propadiene and butynes.

9. The process of claim 1 further comprising subjecting said purified effluent to a selective hydrogenation reaction.

* * * * *